United States Patent [19]

Beer et al.

[11] Patent Number: 5,144,052

[45] Date of Patent: Sep. 1, 1992

[54] REDOX RESPONSIVE ANION RECEPTORS

[75] Inventors: Paul D. Beer; Jana Hodacova; Sally Stokes, all of Oxford, England

[73] Assignee: Metre International, Inc., Westminster, Colo.

[21] Appl. No.: 752,789

[22] Filed: Aug. 30, 1991

[51] Int. Cl.$^5$ .................. C07F 15/06; C07C 15/12
[52] U.S. Cl. .................. 556/144; 556/143; 556/145
[58] Field of Search ............... 556/144, 143, 145, 138

[56] References Cited

U.S. PATENT DOCUMENTS

| | | | |
|---|---|---|---|
| 3,306,917 | 2/1967 | Shapiro et al. | 556/143 |
| 3,853,943 | 12/1974 | Webster | 556/144 X |
| 4,320,066 | 3/1982 | Bertossa | 556/143 |
| 4,656,299 | 4/1987 | Fujii et al. | 556/145 X |
| 4,767,873 | 8/1988 | Katz et al. | 556/143 X |
| 5,021,599 | 6/1991 | Beer et al. | 556/143 X |

Primary Examiner—Arthur C. Prescott
Attorney, Agent, or Firm—Kyle W. Rost

[57] ABSTRACT

A class of ligands capable of solution recognition of anions is defined by a cobalticinium moiety and an adjacent —CO—NH-amide linkage. This class is formed of redox responsive anion receptors, wherein the cobalticinium moiety is acyclic or macrocyclic.

12 Claims, 9 Drawing Sheets

MODEL 1:

Fig.6

MODEL 3:

Fig.7

MODEL 2:

REDOX RESPONSIVE ANION RECEPTORS

TECHNICAL FIELD

The invention generally relates to organic chemistry and organic compounds. More specifically, the invention relates to heavy metal containing compounds, especially to those containing iron, cobalt, or nickel. The synthesis, anion coordination, electrochemistry, and method of use of a redox responsive class of anion receptor, acyclic and macrocyclic polycobalticinium based systems is disclosed.

BACKGROUND ART

The molecular recognition of anionic guest species by positively charged or electron deficient neutral abiotic organic receptor molecules is a relatively new area of chemical investigation. Only a few classes of anion receptor ligands have been reported, including Lewis acid-containing ligands, ammonium quaternary salts, protonated polyamines, and guanidines. The latter positively charged pH-dependent class of host form strong and sometimes selective complexes with a variety of anions including the binding of linear dicarboxylates with chain length selectivity.

In relevant patent art, U.S. Pat. No. 5,021,599 discloses class of redox responsive anion receptors that include the $(C_5H_4)_2M^+$ moiety as part of a macrocycle host structure that is capable of binding an anionic guest, where M is a metal ion having at least two valence states, and the host is capable of complexing with a larger fraction of the guest when M is in one of the valance states as compared to the other.

It would be desirable to produce a redox responsive class of anion receptor, especially of acyclic and macrocyclic polycobalticinium based systems.

It would be further desirable to produce a redox responsive class of anion receptor that achieves solution recognition of anions.

To achieve the foregoing and other objects and in accordance with the purpose of the present invention, as embodied and broadly described herein, the class of compounds, method of manufacture, and method of use of this invention may comprise the following.

DISCLOSURE OF INVENTION

Against the described background, it is therefore a general object of the invention to provide a class of redox responsive anion receptors.

A related object is to provide for the solution recognition of anions.

Additional objects, advantages and novel features of the invention shall be set forth in part in the description that follows, and in part will become apparent to those skilled in the art upon examination of the following or may be learned by the practice of the invention. The object and the advantages of the invention may be realized and attained by means of the instrumentalities and in combinations particularly pointed out in the appended claims.

According to the invention, a class of ligands capable of solution recognition of anions is defined by a cobalticinium moiety and an adjacent —CO—NH— amide linkage. This class is formed of redox responsive anion receptors, wherein the cobalticinium moiety is acyclic or macrocyclic. The anion selectivity of the class is believed to be achieved by the nature of a group attached to the amide linkage.

The accompanying drawings, which are incorporated in and form a part of the specification illustrate preferred embodiments of the present invention, and together with the description, serve to explain the principles of the invention. In the drawings:

BEST MODE FOR CARRYING OUT THE INVENTION

Figure 1:
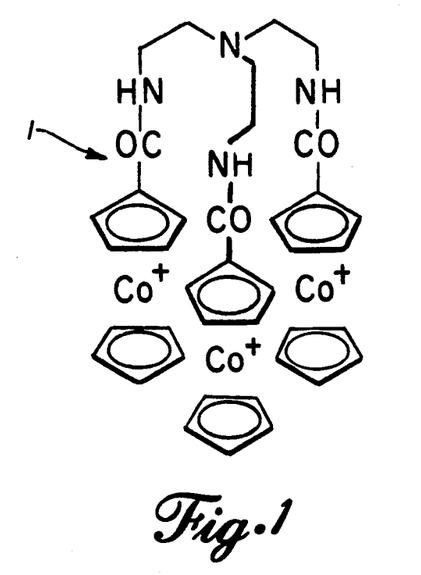
FIG. 1 is a structure of a member of the class.
Figure 2:
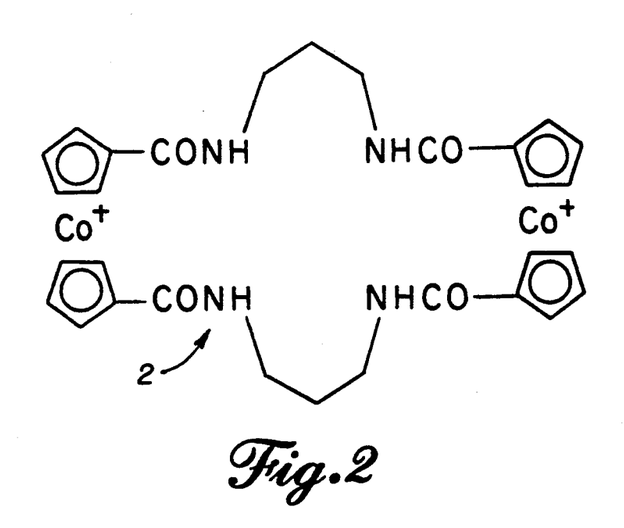
FIG. 2 is another structure of a member of the class.

The invention resides in the creation and use of a cobalticinium moiety in combination with an adjacent —CO—NH—amide linkage in order to achieve the solution recognition of anions. This class of receptors has typical structures shown as the anion coordinating units of (1) and (2), shown in FIGS. 1 and 2.

EXAMPLE 1

The addition of axmonium chloride and bromide to deuterated acetonitrile $^1H$ n.m.r. solutions of (1) and (2) resulted in large shifts of the respective protons of both receptors. Of particular note are the substantial downfield shifts of the amide protons ($\partial = 1.52$ ppm for (1)) which suggests a significant CO—NH····anion interaction. Cathodic shifts of the respective hosts' reversible reduction wave occur on addition of stoiohiometric amounts of chloride and bromide to electrochemical solutions of (1)-(2).

EXAMPLE 2

Figure 3:
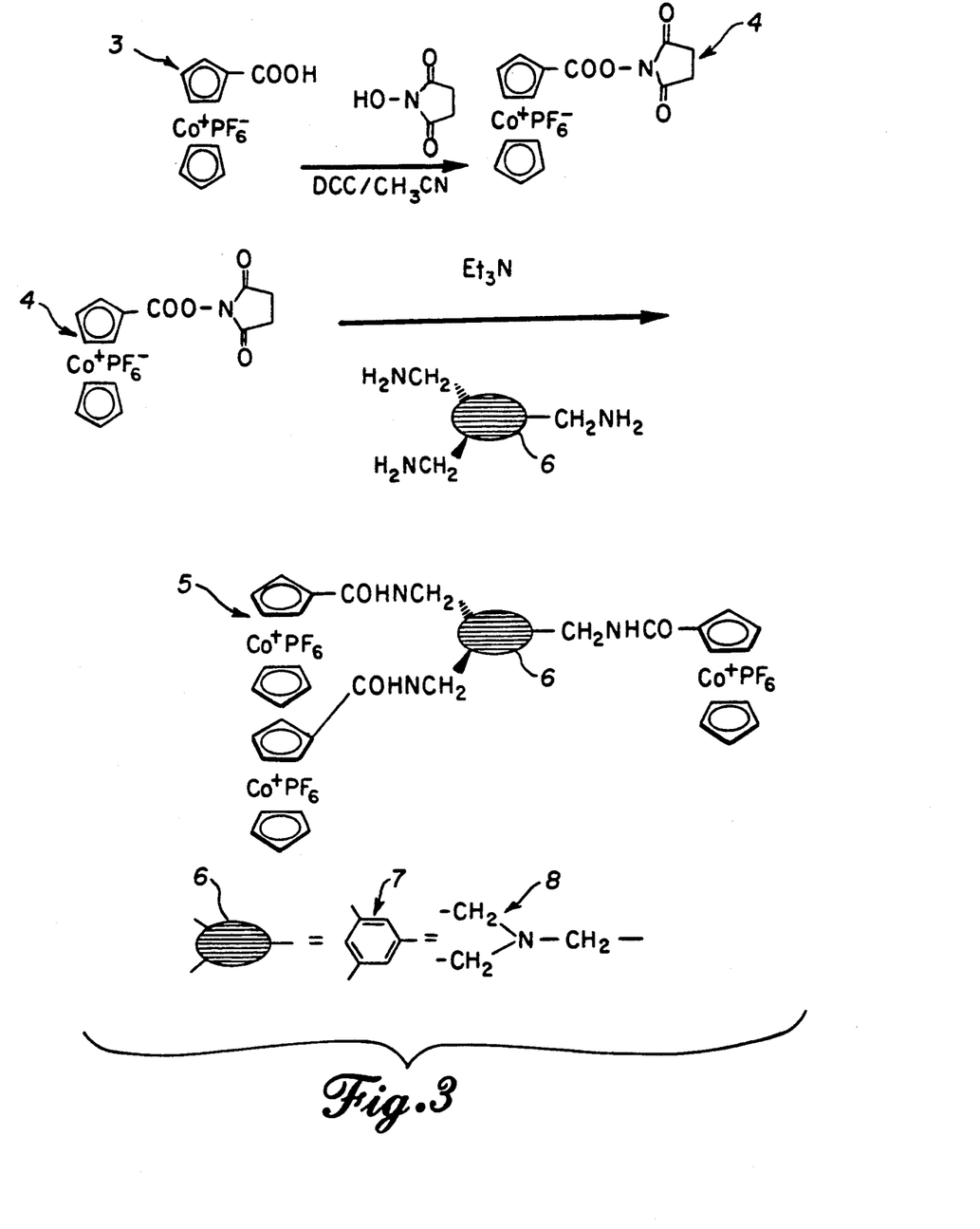
FIG. 3 is a scheme for synthesis of the structures of FIGS. 1 and 2.
Figures 4, 5:
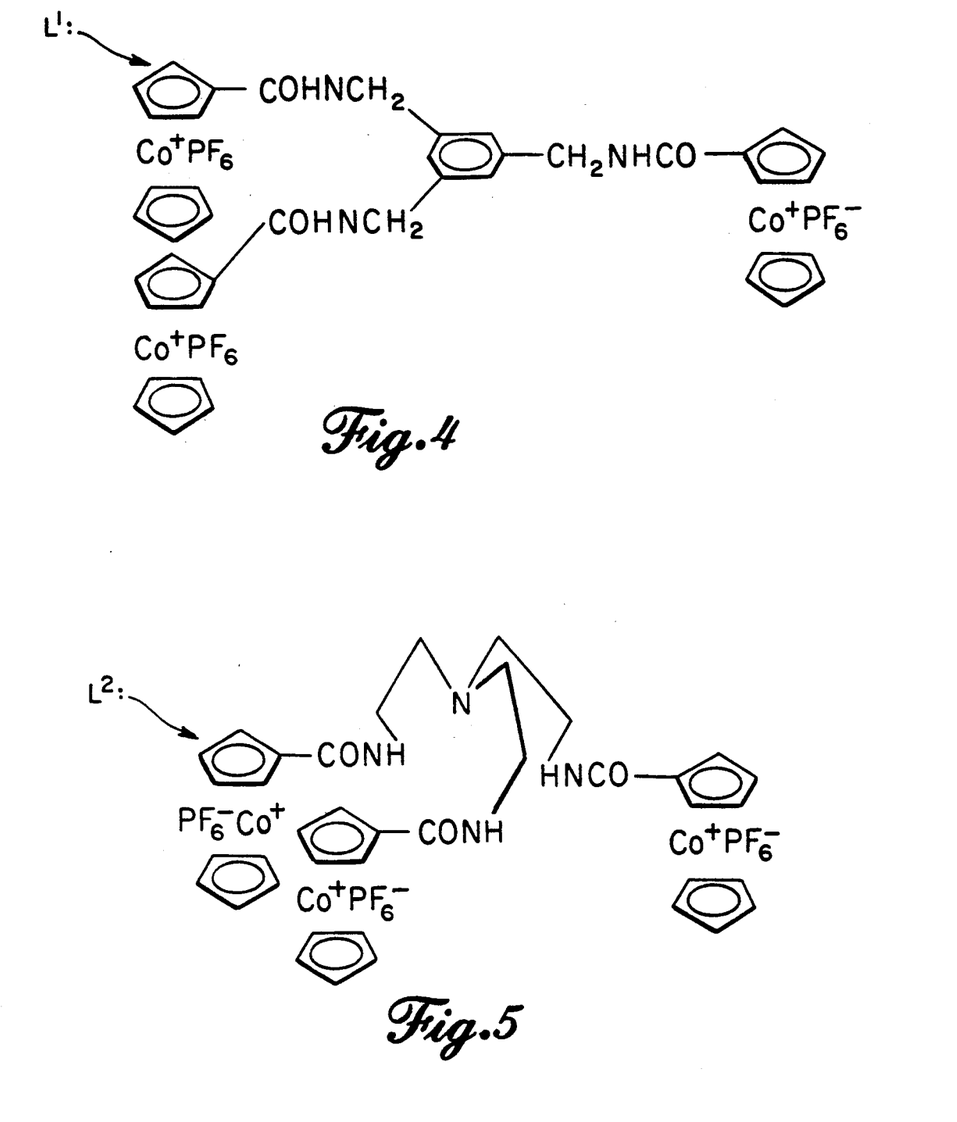
FIG. 4 is the structure of a product of the scheme of FIG. 3.
FIG. 5 is the structure of a product of the scheme of FIG. 3.

The following example illustrates the syntheses of derivatives. FIG. 3 shows the preparation of $PF_6^-$ salts of the cobalticinium moiety, starting with (3) and producing (4) and (5). The identity of molecular fragment (6) is variable and may be either (7) or (8). In the event that the fragment is (7), then the product is ($L^1$), as shown in FIG. 4. In the event that the fragment is (8), then the product is ($L^2$), as shown in FIG. 5.

In a representative synthesis of ($L^2$), a solution of 1 mmol of (4) in dry $CH_3CN$ and 0.34 mmol tren and 1.6 mmol Et$_3$N was stirred at room temperature for 18 hours. Evaporation of solvent and chromatography on Sephadox LM20 using CH$_3$CN as eluent gave the desired product in 60% yield.

In a representative synthesis of (L$^1$), an analogous procedure was employed using mesitylene triamine instead of tren. The procedure gave the desired product in 65% yield.

EXAMPLE 3

$^1$H n.m.r. studies were conducted for product L$^1$ with the following results.

| $^1$H-NMR DOWNFIELD SHIFTS OF L$^1$ IN CD$_3$CN (ADDITION OF 1 EQ. OF ANION) | | | | | |
|---|---|---|---|---|---|
| | F$^-$ | Cl$^-$ | Br$^-$ | NO$_3^-$ | BF$_4^-$ |
| —NH—CO— | 2.48 | 1.28 | 1.02 | 0.60 | 0.02 |
|  | 0.29 | 0.31 | 0.30 | 0.15 | 0.01 |

| $^1$H-NMR DOWNFIELD SHIFTS OF L$^1$ IN d$_6$-DMSO (ADDITION OF 1 EQ. OF ANION) | | | |
|---|---|---|---|
| | F$^-$ | Cl$^-$ | NO$_3^-$ |
| —NH—CO— | 1.48 | 0.27 | 0.02 |
|  | 0.17 | 0.08 | 0.00 |

EXAMPLE 4

$^1$H n.m.r. studies were conducted for product L$^2$ with the following results.

| $^1$H-NMR DOWNFIELD SHIFTS OF L$^2$ IN CD$_3$CN (ADDITION OF 1 EQ. OF ANION) | | | |
|---|---|---|---|
| | Cl$^-$ | Br$^-$ | NO$_3^-$ |
| —NH—CO— | 1.52 | 0.91 | 0.58 |
|  | 0.36 | 0.27 | 0.13 |

| $^1$H-NMR DOWNFIELD SHIFTS OF L$^2$ IN d$_6$-DMSO (ADDITION OF 1 EQ. OF ANION) | | |
|---|---|---|
| | Cl$^-$ | F$^-$ |
| —NH—CO— | 0.38 | 2.20 |
|  | 0.11 | 0.33 |

EXAMPLE 5

Figure 6:
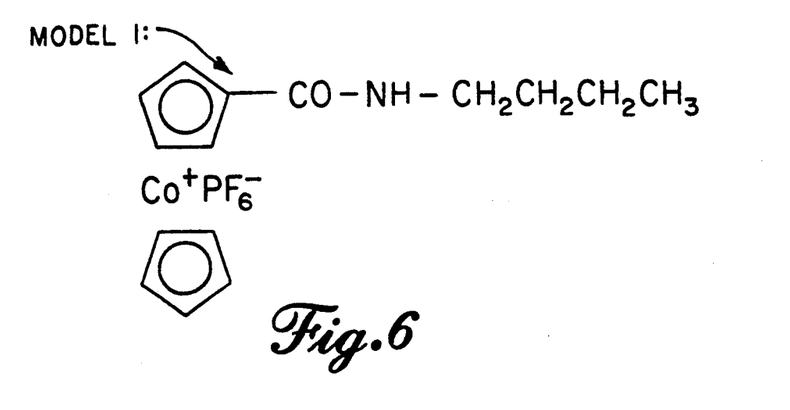
FIG. 6 is the structure of a model compound.
Figure 7:
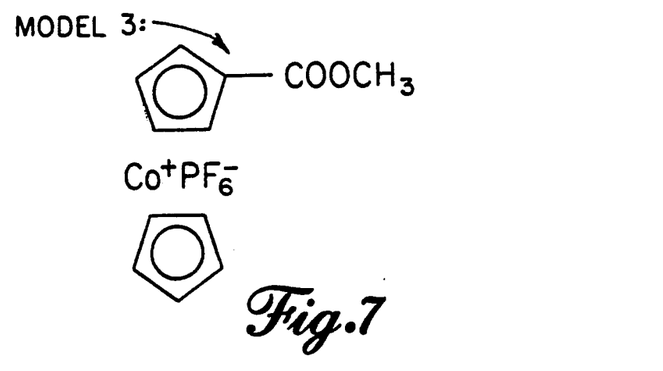
FIG. 7 is the structure of another model compound.
Figure 8:
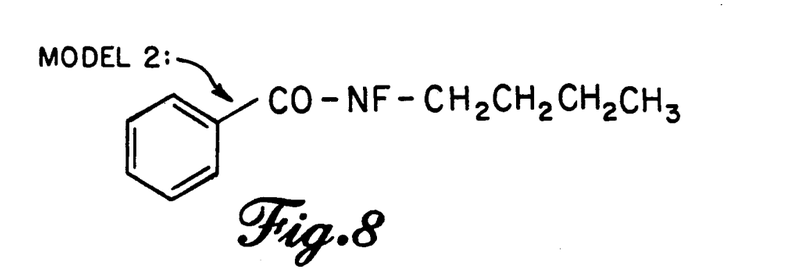
FIG. 8 is the structure of another model compound.
Figure 14:
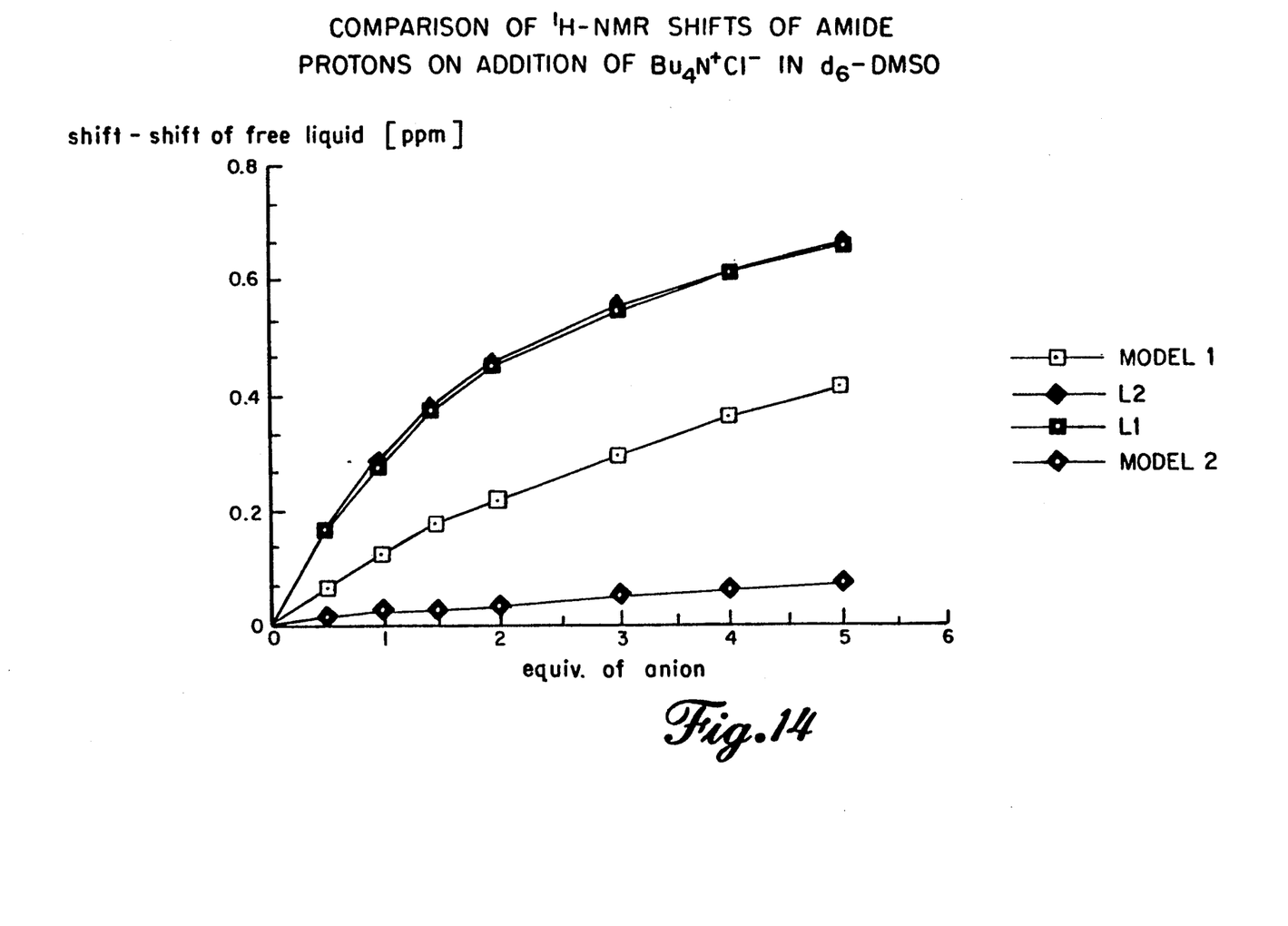
FIG. 14 is a graph of comparative $^1H$ n.m.r. shifts of amide protons.

Referring to FIG. 6, 8, and 7, respectively, compounds Model 1, Model 2, and Model 3 were prepared. Model 1, Model 2, product L$^1$, and L$^2$ were compared as to $^1$H n.m.r. shifts of amide protons on addition of Bu$_4$N$^+$Cl$^-$ in d$_6$—DMSO, with the results shown in FIG. 14.

EXAMPLE 6

Figure 13:
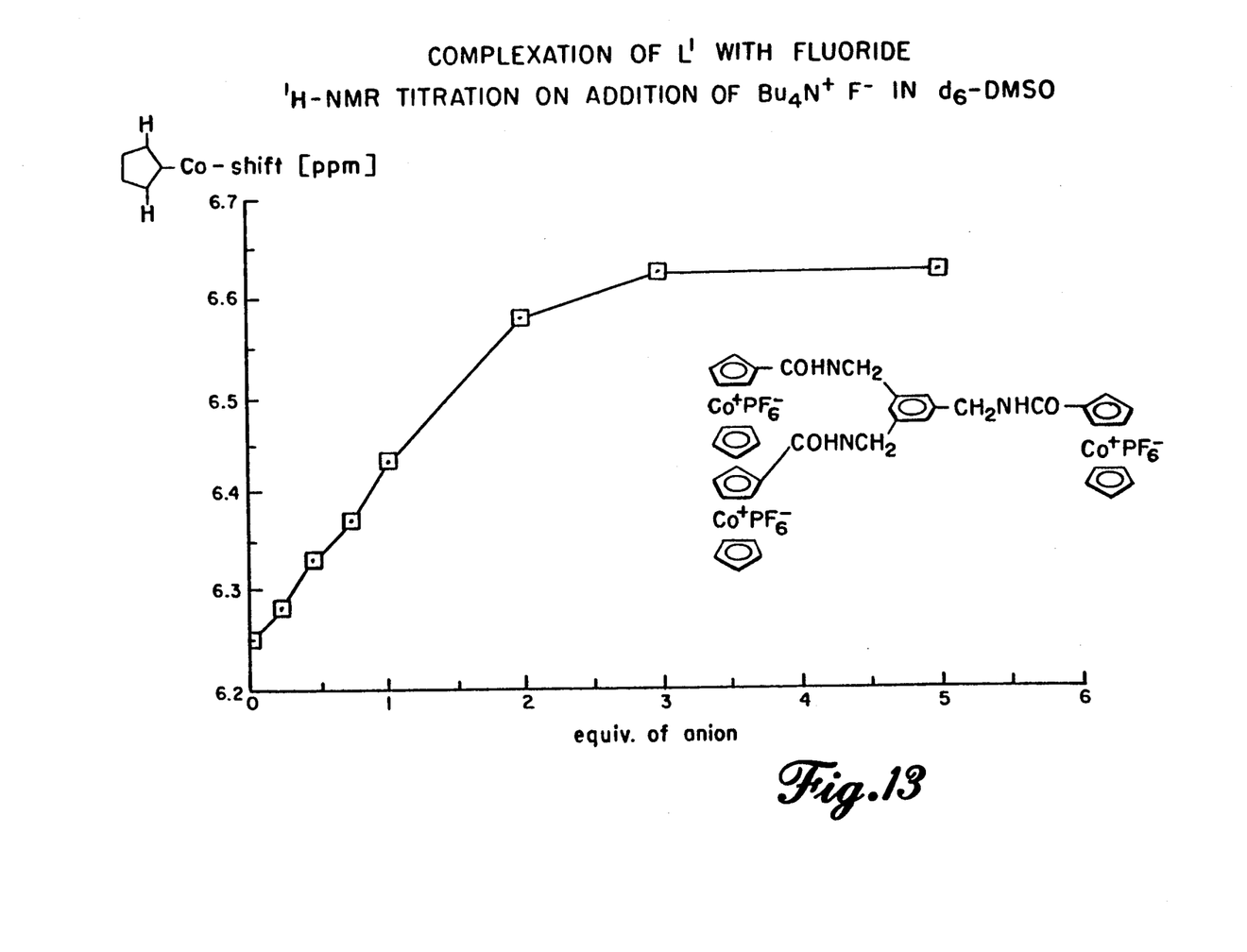
FIG. 13 is a graph of $^1H$ n.m.r. titration curves with respect to fluoride.

Complexation of product L$^1$ with fluoride was studied by $^1$H n.m.r. titration on addition of Bu$_4$N$^+$Cl$^-$ in d$_6$—DMSO, with the results shown in FIG. 13.

EXAMPLE 7

Figure 15:
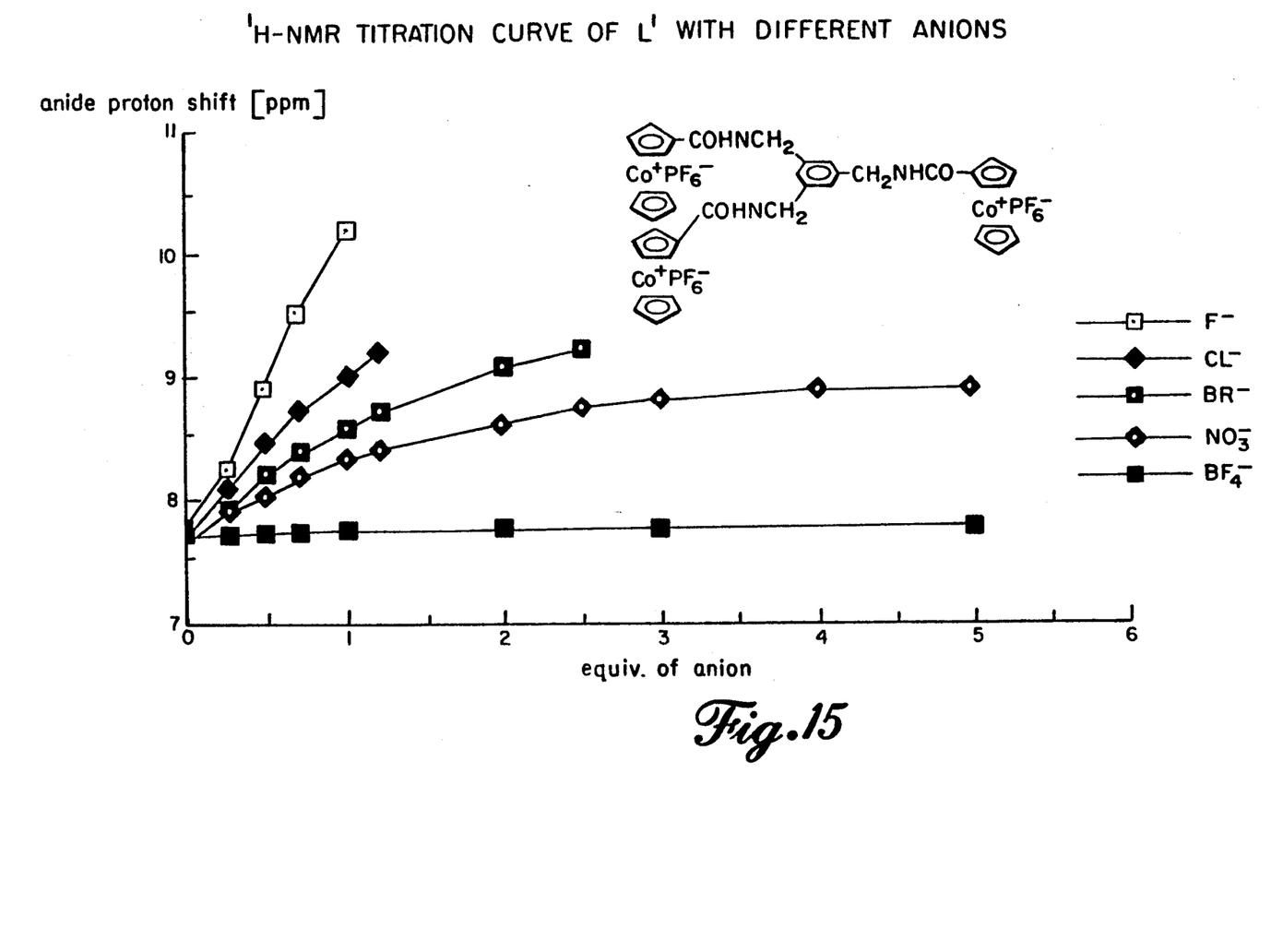
FIG. 15 is a graph of $^1H$ n.m.r. titration curves with respect to different anions.

The $^1$H n.m.r. titration curves of product L$^1$ with respect to different anions, specifically F$^-$, Cl$^-$, Br$^-$, NO$_3^-$, and BF$_4^-$, were studied with the results shown in FIG. 15.

EXAMPLE 8

Figure 9:
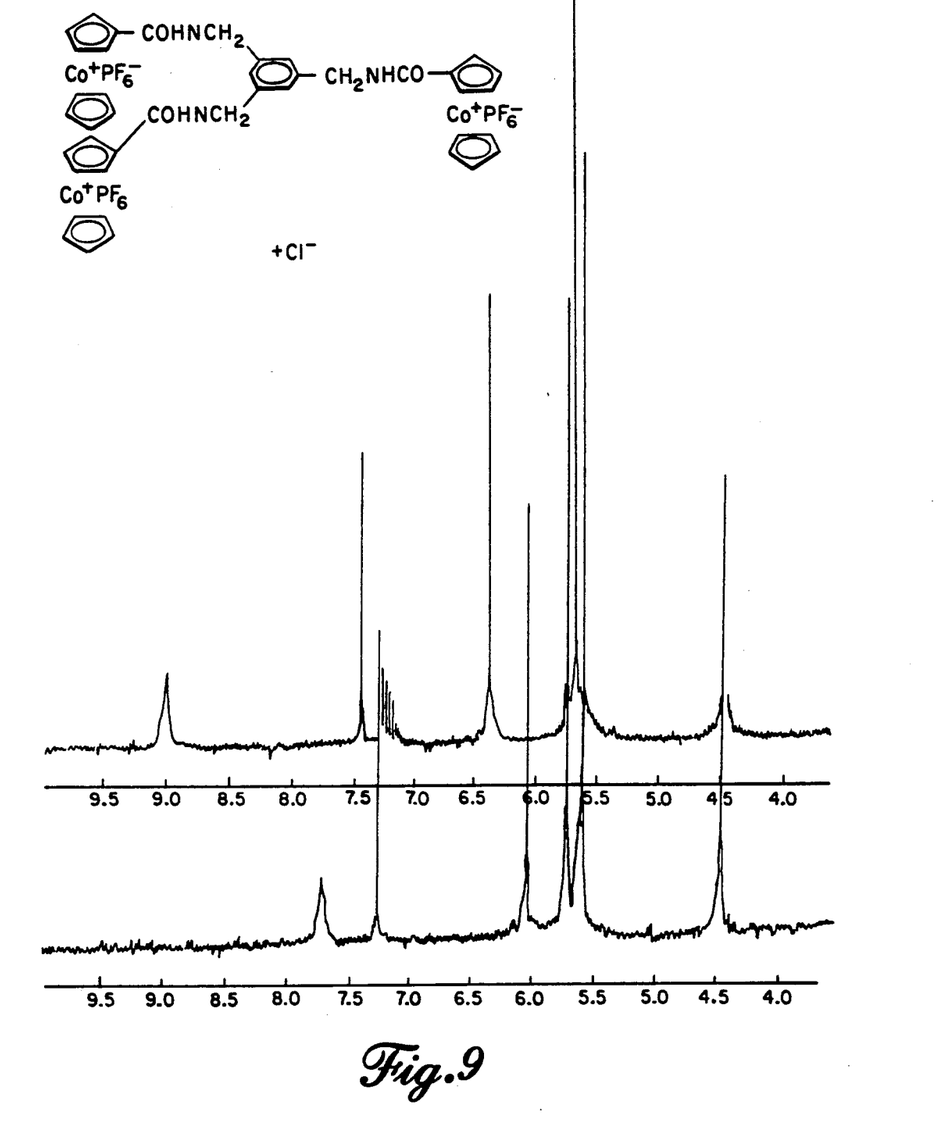
FIG. 9 is an $^1H$ n.m.r. comparative study of the class member illustrated therein when mixed with chloride ion.

$^1$H n.m.r. studies of L$^1$ with the addition of Cl$^-$ produced the comparative readings of FIG. 9.

EXAMPLE 9

The electrochemistry of products L$^1$ and L$^2$ was studied with respect to different ions in different solvents, with the following results.

| ELECTROCHEMISTRY CATHODIC SHIFTS OF REVERSIBLE REDUCTION WAVE UPON THE ADDITION OF ANION | | |
|---|---|---|
| L$^1$ | F$^-$ | 55 mV in DMSO |
| | Cl$^-$ | 30 mV in CH$_3$CN |
| | NO$_3^-$ | 10 mV in CH$_3$CN |
| L$^2$ | F$^-$ | 45 mV in CH$_3$CN* |
| | | 60 mV in DMSO |
| | Cl$^-$ | 20 mV in CH$_3$CN |
| | NO$_3^-$ | no shift |

*precipitation problems

EXAMPLE 10

Figure 11:
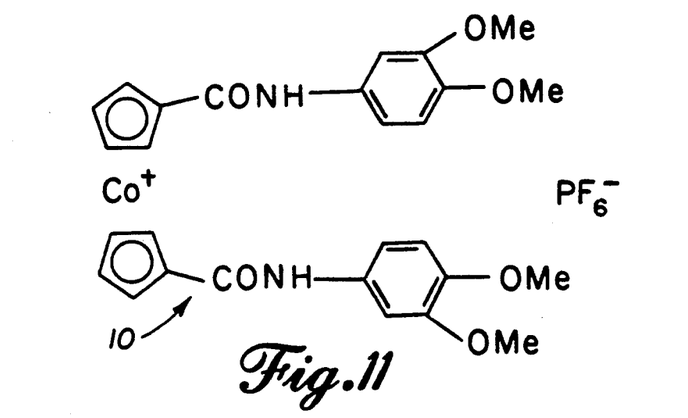
FIG. 11 is the structure of another member of the class.

The product 10 shown in FIG. 11 was prepared by combination of 1.24 g. (27 mmol) of 1,1'-bis(chlorocarbonyl) cobalticinium chloride added to 0.83 g. (54 mmol) of 4-aminoveratrole in the presence of 1.5 g. Et$_3$N in 40 ml of dry CH$_3$CN. The reaction mixture was stirred at room temperature for 12 hours. Chromatography on Sephadex column using methanol as eluent followed by addition of an excess of NH$_4$PF$_6$ gave the desired product in 55% yield. It was found that product (10) coordinates anions.

Figure 10:
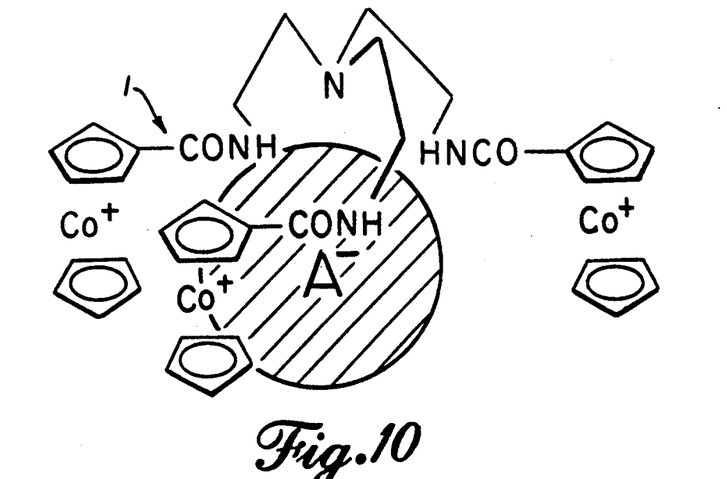
FIG. 10 is a schematic drawing of the method by which the class complexes with an anion.
Figure 12:
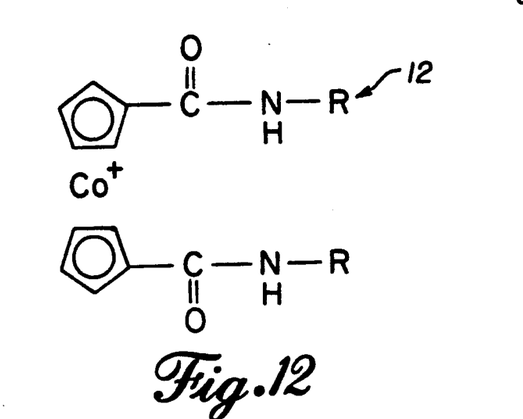
FIG. 12 is a generalized structure of members of the class.

Model ligand (1) also is successful in complexing anions. The relationship of the ligand to the guest anion is shown in FIG. 10, where the anion A$^-$ is received in the cavity of the host ligand. It appears that the amide unit must be hydrogen bonding to the complexed anion. Analogous systems lacking the amide unit do not coordinate anions. It is believed that selectivity may be achieved via the nature of the R group in the generalized moiety (12) in FIG. 12. Thus, R may be, for example, any alkyl or aryl group.

The foregoing is considered as illustrative only of the principles of the invention. Further, since numerous modifications and changes will readily occur to those skilled in the art, it is not desired to limit the invention to the exact construction and operation shown and described, and accordingly all suitable modifications and equivalents may be regarded as falling within the scope of the invention as defined by the claims that follow.

We claim:

1. A class of ligands capable of solution recognition of anions, wherein each ligand comprises:
   a cobalticinium moiety; and
   an adjacent —CO—NH— amide linkage.

2. The class of ligands of claim 1, wherein said cobalticinium moiety is an acyclic cobalticinium based system.

3. The class of ligands of claim 1, wherein said cobalticinium moiety is a macrocyclic cobalticinium based system.

4. The class of ligands of claim 1, wherein one member consists of

5. The class of ligands of claim 1, wherein one member consists of

6. The class of ligands of claim 1, wherein one member consists of

7. The class of ligands of claim 1, wherein one member consists of

8. The class of ligands of claim 1, wherein one member consists of and R is chosen from the group consisting of alkyl and aryl.

9. The method of removing a selected ion from solution, comprising adding to the solution a ligand having a cobalticinium moiety and an adjacent —CO—NH— amide linkage capable of solution recognition of a selected anion.

10. The method of claim 9, wherein said moiety is an acyclic cobalticinium based system.

11. The method of claim 9, wherein said moiety is a macrocyclic cobalticinium based system.

12. A class of ligands capable of solution recognition of anions, wherein each ligand consists of at least:
   a cobalticinium moiety and an adjacent —CO—NH— amide linkage as part of a host structure, wherein said host structure defines a cavity capable of binding an anionic guest; and
   an anionic guest bound within said cavity.

* * * * *